United States Patent
Nakanishi et al.

(10) Patent No.: US 9,541,508 B2
(45) Date of Patent: Jan. 10, 2017

(54) INSPECTING DEVICE AND INSPECTING METHOD

(71) Applicants: DAINIPPON SCREEN MFG. CO., LTD., Kyoto-shi, Kyoto (JP); OSAKA UNIVERSITY, Suita-shi, Osaka (JP)

(72) Inventors: Hidetoshi Nakanishi, Kyoto (JP); Akira Ito, Kyoto (JP); Masayoshi Tonouchi, Suita (JP); Iwao Kawayama, Suita (JP)

(73) Assignees: SCREEN HOLDINGS CO., LTD., Kyoto (JP); OSAKA UNIVERSITY, Osaka (JP)

(*) Notice: Subject to any disclaimer, the term of this patent is extended or adjusted under 35 U.S.C. 154(b) by 154 days.

(21) Appl. No.: 14/201,298

(22) Filed: Mar. 7, 2014

(65) Prior Publication Data
US 2014/0253911 A1    Sep. 11, 2014

(30) Foreign Application Priority Data

Mar. 8, 2013 (JP) ................................. 2013-046225

(51) Int. Cl.
*G01N 21/95* (2006.01)
*G01N 21/63* (2006.01)

(52) U.S. Cl.
CPC ........ *G01N 21/9501* (2013.01); *G01N 21/636* (2013.01); *G01N 21/9505* (2013.01)

(58) Field of Classification Search
CPC .............. G01N 21/9501; G01N 21/956; G01N 21/8806; G01N 21/94; G01N 21/95607; G01N 21/47; G01N 21/636; G01N 21/9505; H01L 2924/0002; H01L 22/12; H01L 2924/00; H01L 21/67288; G06T 2207/30148; G06T 7/001; G06T 7/00
(Continued)

(56) References Cited

U.S. PATENT DOCUMENTS 5,258,612 A * 11/1993 Clark ................... G01N 21/636
                                                    250/226
5,734,470 A *  3/1998 Rogers ................. G01N 21/636
                                                    356/432
(Continued)

FOREIGN PATENT DOCUMENTS

EP    1441233 A1    7/2004
GB    2359619 A     8/2001
(Continued)

OTHER PUBLICATIONS

Extended European Search Report EP Application No. 14153853.8 dated Jun. 30, 2014.

(Continued)

*Primary Examiner* — Tarifur Chowdhury
*Assistant Examiner* — Mohamed K Amara
(74) *Attorney, Agent, or Firm* — McDermott Will & Emery LLP

(57) ABSTRACT

An inspecting device includes: an irradiation part for dividing pulsed light emitted from a femtosecond laser into measurement pump light and measurement probe light, to irradiate a solar cell; a detection part for detecting an electromagnetic wave emitted from the solar cell in accordance with the irradiation with the measurement probe light; and a measurement delay part for delaying the time of arrival of the measurement probe light at the solar cell relatively to the measurement pump light. The irradiation part is provided with a galvano mirror for scanning with the measurement probe light a wide range which is wider than an irradiated range (pump light spot) being irradiated with the measurement pump light in a solar cell.

7 Claims, 17 Drawing Sheets

(58) Field of Classification Search
USPC .................................................. 356/237.5
See application file for complete search history.

(56) References Cited

U.S. PATENT DOCUMENTS

| | | | | |
|---|---|---|---|---|
| 6,317,216 | B1* | 11/2001 | Maris | G01N 21/8422 257/E21.53 |
| 7,593,099 | B2* | 9/2009 | Ohtake | G01N 21/3581 356/237.1 |
| 8,129,683 | B2 | 3/2012 | Itsuji et al. | |
| 8,344,324 | B2 | 1/2013 | Kasai et al. | |
| 2002/0180986 | A1* | 12/2002 | Nikoonahad | G03F 7/70625 356/600 |
| 2004/0085540 | A1* | 5/2004 | Lapotko | G01N 21/171 356/432 |
| 2004/0207850 | A1* | 10/2004 | Kwak | G01N 21/636 356/432 |
| 2004/0235205 | A1* | 11/2004 | Levy | G01N 21/211 438/14 |
| 2004/0246011 | A1* | 12/2004 | Tonouchi | G01R 31/311 324/754.23 |
| 2007/0235650 | A1* | 10/2007 | Federici | G01J 3/42 250/341.8 |
| 2008/0160090 | A1* | 7/2008 | Oraevsky | A61K 41/0052 424/489 |
| 2010/0088787 | A1* | 4/2010 | Shigekawa | B82Y 35/00 850/6 |
| 2010/0252738 | A1 | 10/2010 | Kasai et al. | |
| 2011/0216312 | A1 | 9/2011 | Matsumoto et al. | |
| 2013/0083319 | A1* | 4/2013 | Nakanishi | G01N 21/1717 356/237.5 |
| 2013/0129568 | A1* | 5/2013 | Gusev | G01N 21/59 422/82.09 |
| 2014/0239182 | A1* | 8/2014 | Ito | G01N 21/63 250/351 |
| 2016/0043008 | A1* | 2/2016 | Murray | G01N 29/2418 438/5 |

FOREIGN PATENT DOCUMENTS

| | | |
|---|---|---|
| JP | 04-009641 A | 1/1992 |
| JP | 2004-349582 A | 12/2004 |
| JP | 2009-150873 A | 7/2009 |
| JP | 2009-175127 A | 8/2009 |
| JP | 2010-60317 A | 3/2010 |
| JP | 2013-19861 | 1/2013 |

OTHER PUBLICATIONS

Masayoshi Tonouchi et al., "Pump and Probe Terahertz Generation Study of Ultrafast Carrier Dynamics in Low-Temperature Grown-GaAs", Jpn. J. Appl. Phys, vol. 41, Jun. 15, 2002, pp. L706-L709.

Kouhei Takahashi et al., "Ultrafast carrier dynamics of charge-ordered manganite Pr0.7Ca0.3MnO3 studied by pump-probe terahertz emission spectroscopy", Physica B 359-361 (2005) pp. 1282-1284.

Y. Shimada et al., "Time-resolved terahertz emission spectroscopy of wide miniband GaAs/AlGaAs superlattices", Applied Physics Letters, vol. 81, No. 9, Aug. 26, 2002, pp. 1642-1644.

Taiichi Otsuji et al., "Spectroscopic Study on Ultrafast Carrier Dynamics and Terahertz Amplified Stimulated Emission in Optically Pumped Graphene", J. Infrared Milli Terahz Waves (2012) 33:825-838.

Shogo Fujiwara, et al; "Study of Carrier Dynamics in LT-GaAs Photoconductive Switch Using Pump-Probe Laser Terahertz Emission Microscope"; IEICE Technical Report. ED 110 (342), pp. 87-90, Dec. 9, 2010.

Japanese Office Action dated Aug. 9, 2016 issued in Japanese Patent Application No. 2013-046225 with English translation.

Japanese Decision of Grant dated Oct. 25, 2016 issued in Japanese Patent Application No. 2013-046225 (with English machine translation).

* cited by examiner

F I G . 1
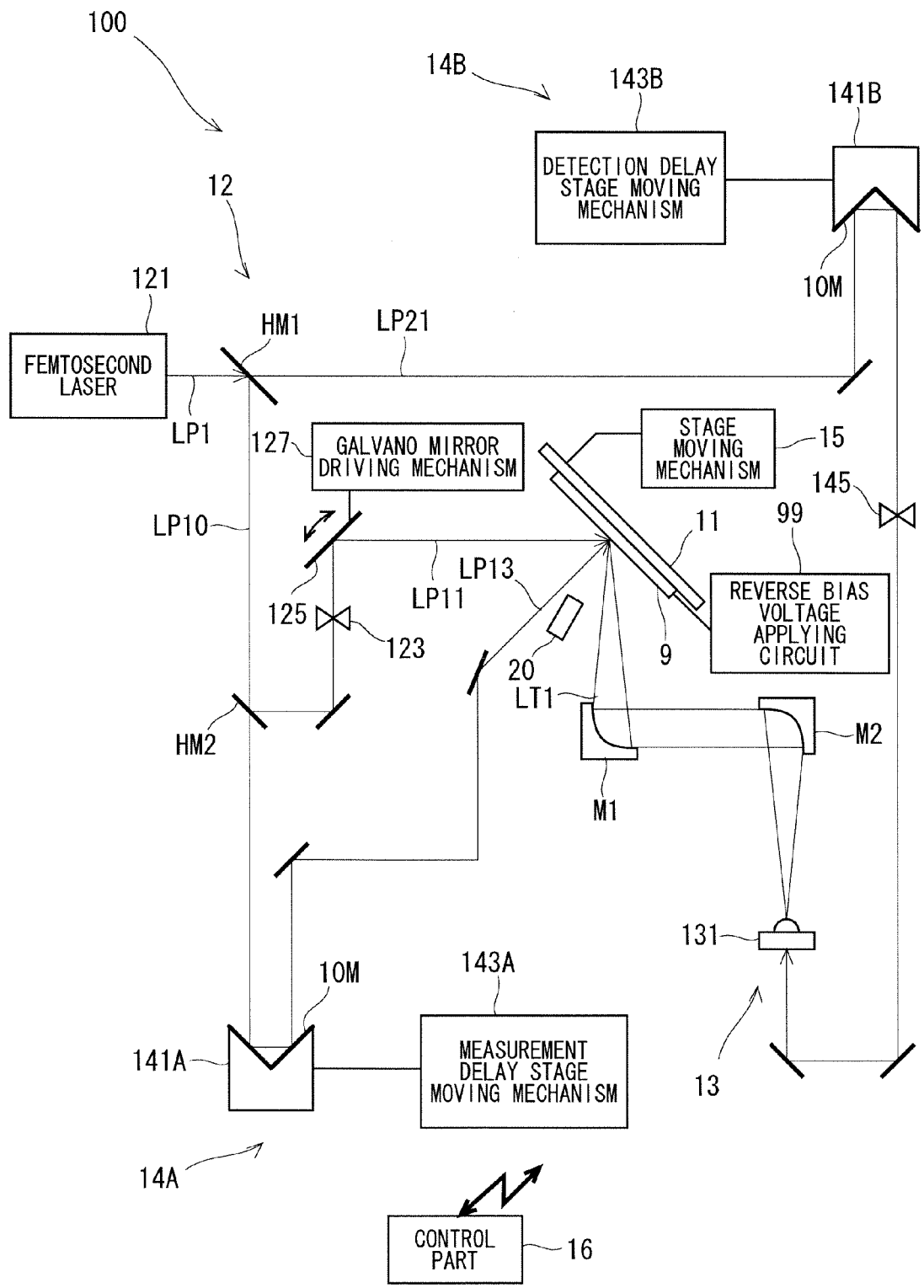

F I G . 3
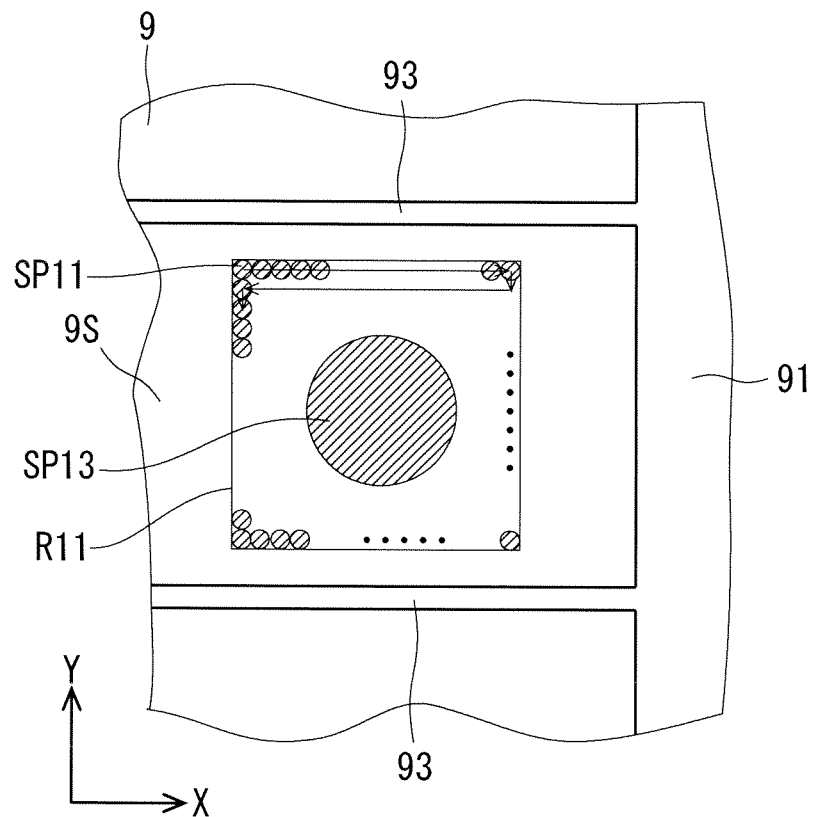

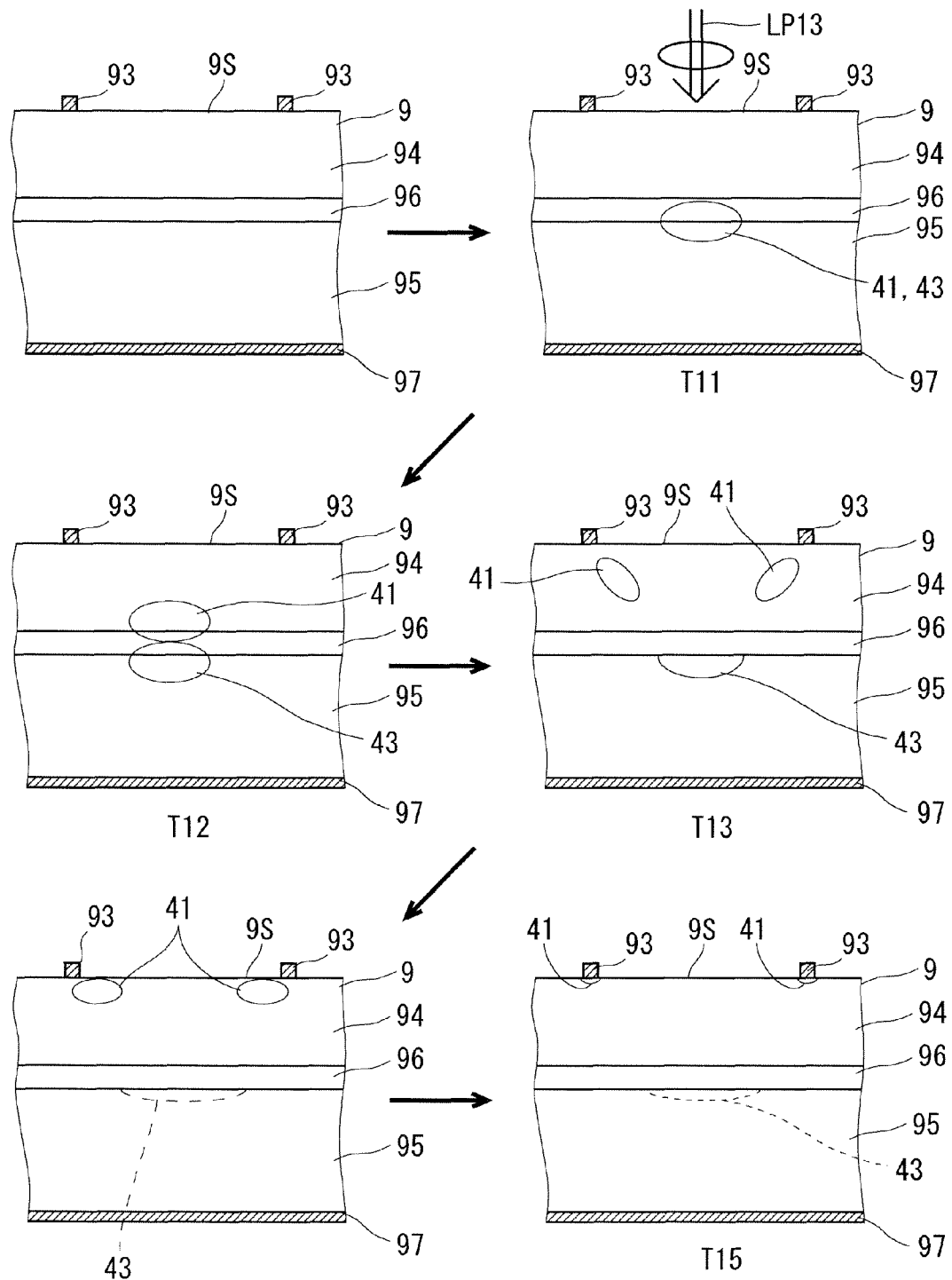
F I G . 6

F I G . 1 0
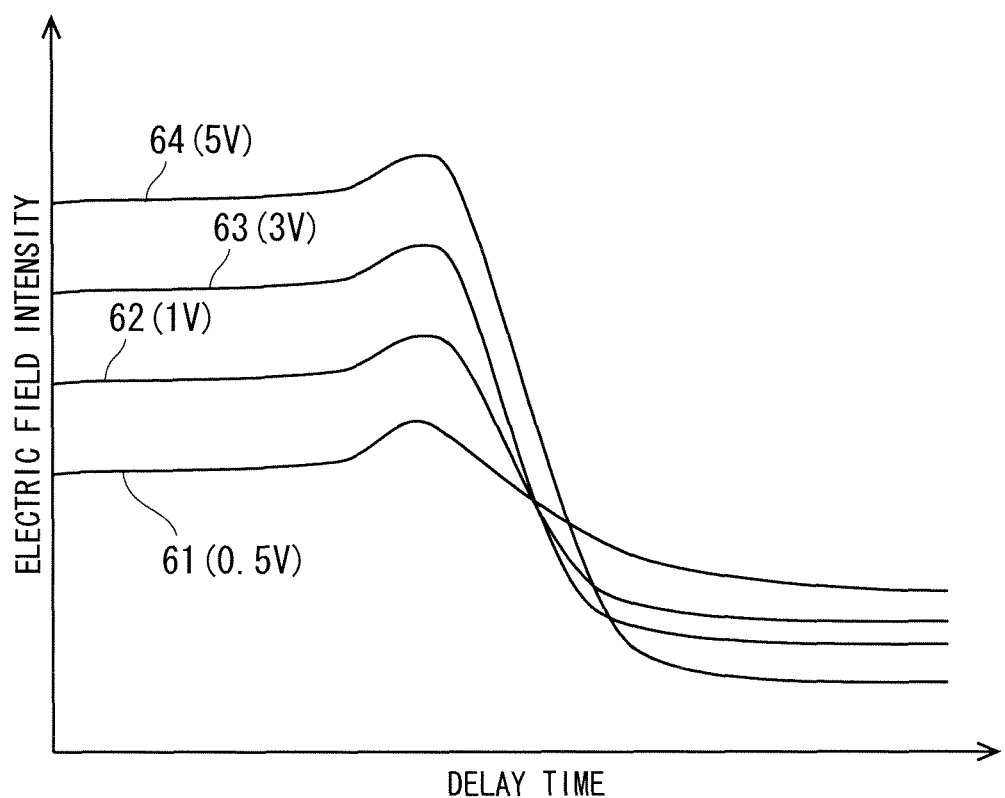

F I G . 1 4
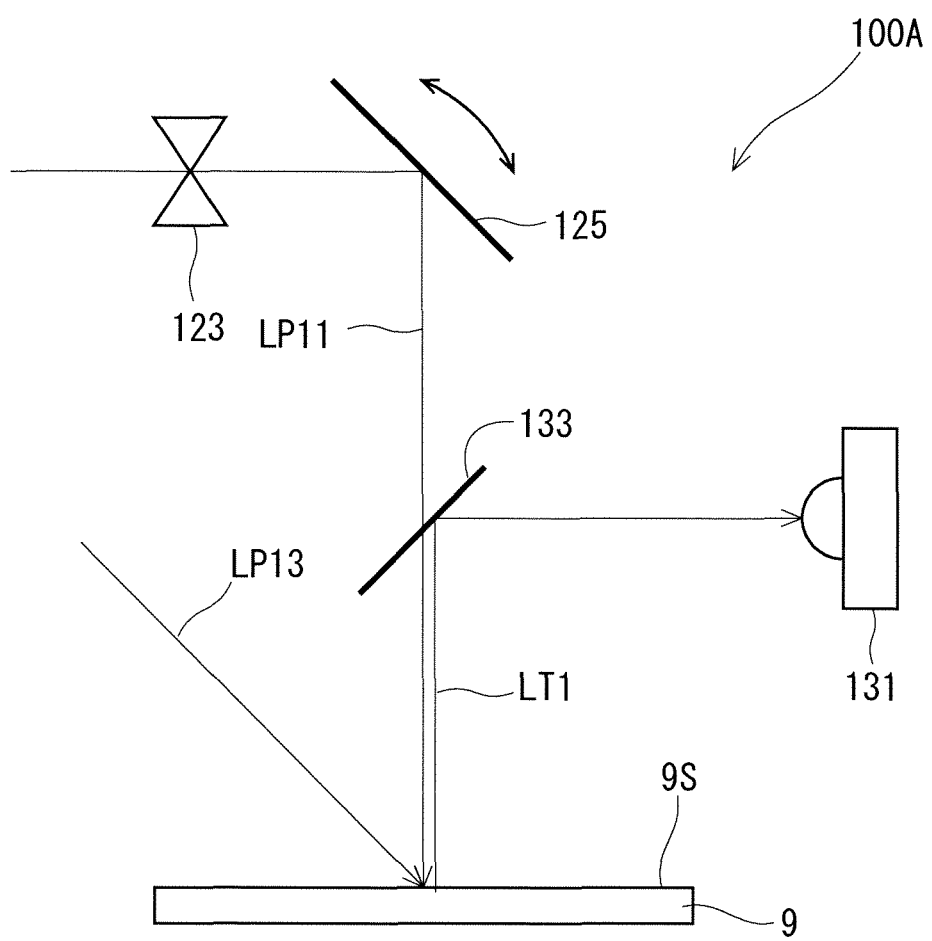

F I G . 1 6
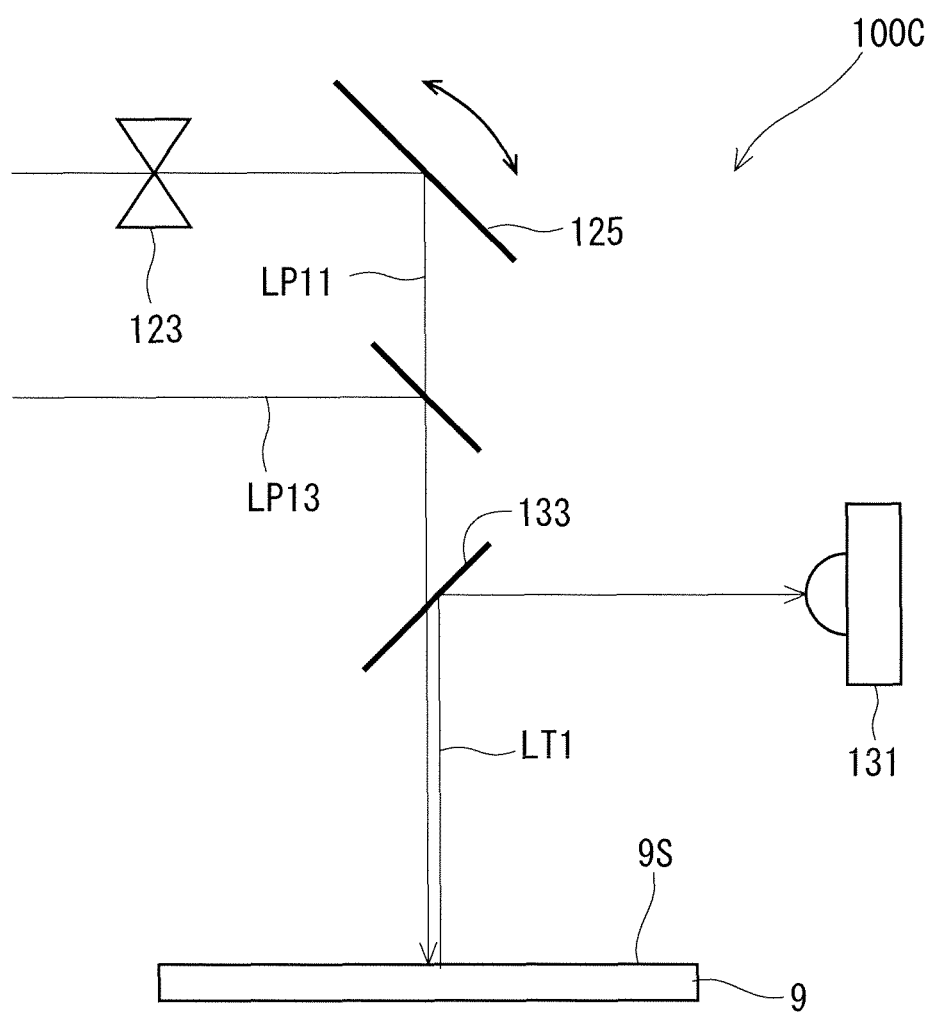

INSPECTING DEVICE AND INSPECTING METHOD

BACKGROUND OF THE INVENTION

Field of the Invention

The present invention relates to a technique for inspecting a semiconductor device or a photo device.

Description of the Background Art

There is already known a semiconductor inspecting device which detects an electromagnetic wave emitted from a semiconductor device when irradiating it with pulsed laser light, thereby to inspect the semiconductor device in non-contact (Japanese Patent Application Laid-Open No. 2010-60317).

Further, the present applicant has proposed a technique of irradiating a photo device with pulsed light and detecting an electromagnetic wave emitted from the photo device accordingly, thereby to inspect the photo device (Japanese Patent Application Laid-Open No. 2013-19861).

Moreover, there has already been proposed a technique of scanning with probe light the inside of a region irradiated with pump light by using pump-probe measurement to make photoexcited carriers visible ("Study of Carrier Dynamics in LT-GaAs Photoconductive Switch Using Pump-Probe Laser Terahertz Emission Microscope", Shogo Fujiwara, et al., IEICE Technical Report. ED 110(342), 87-90, 2010-12-09). Specifically, it is described that by using a photoconductive switch being a representative terahertz wave generating device as a sample, dynamics of photoexcited carriers are observed at a subpicosecond temporal resolution and a several-micrometer spatial resolution.

Inspecting the processes of generation, movement and disappearance of the photoexcited carriers on the subpicosecond level in the semiconductor device or the photo device gives extremely precious information in inspecting performance or a defect of those. In particular, in the photo device, analyzing generation of the photoexcited carriers, the lifetime thereof after the generation to recombination, movement thereof to the electrode, and the like can give extremely important information in evaluating performance or a defect of the photo device. However, a technique of detecting the dynamics of the photoexcited carriers in the photo device is unknown.

Moreover, in the report by Fujiwara et al., only the inside of the region irradiated with the pump light is irradiated with the probe light. There has thus been a problem of not being able to inspect photoexcited carriers which are generated, move or disappear out of the region with the pump light.

SUMMARY OF THE INVENTION

The present invention is directed to an inspecting device for taking a semiconductor device or a photo device as an inspecting target.

A first aspect is an inspecting device which takes a semiconductor device or a photo device as an inspecting target, the device including: an irradiation part for irradiating the inspecting target with each of pump light and probe light having the same pulse period; a detection part for detecting an electromagnetic wave emitted from the inspecting target in accordance with the irradiation with the probe light; and a measurement delay part for delaying the time of arrival of the probe light at the inspecting target relatively to the pump light, wherein the irradiation part is provided with a scanning mechanism to scan with the probe light a wide range which is wider than an irradiated range being irradiated with the pump light in the inspecting target.

Therefore, even a region not being irradiated with the pump light can be observed in terms of generation, movement, recombination, disappearance and the like of photoexcited carriers by pump-probe measurement. It is thereby possible to perform more detailed inspection on performance or a defect of the semiconductor device or the photo device.

A second aspect is the inspecting device according to the first aspect which further includes an image generation part for generating an image indicating electric field intensity distribution of the electromagnetic wave detected by the detection part.

It is therefore possible to image the electric field intensity distribution in the inspecting target.

A third aspect is the inspecting device according to the first or second aspect which further includes an irradiated position changing part for changing a position irradiated with the pump light.

It is therefore possible to perform the pump-probe measurement in an arbitrary position of the inspecting target.

In a fourth aspect being the inspecting device according to any one of the first to third aspects, the detection part is provided with a detector for receiving detection pulsed light having the same pulse period as the probe light, to detect an electromagnetic wave generated in accordance with the irradiation with the probe light, and the inspecting device further includes a detection delay part for delaying the time of arrival of the detection pulsed light at the detector relatively to the time of arrival of the electromagnetic wave at the detector.

It is therefore possible to restore a temporal waveform as to the electromagnetic wave emitted in accordance with the irradiation with the probe light.

A fifth aspect is the inspecting device according to any one of the first to fourth aspects, which further includes a reverse bias voltage applying part for applying a reverse bias voltage.

Further, according to the fifth aspect, applying a reverse bias voltage can lead to enhancement of the intensity of the emitted electromagnetic wave.

In a sixth aspect being the inspecting device according to the fifth aspect, a reverse bias voltage applied by the reverse bias voltage applying part is variable.

According to the sixth aspect, it is possible to apply a reverse bias voltage having so a suitable magnitude as not to hinder the pump-probe measurement in accordance with a set inspection range.

Further, the present invention is directed to an inspecting method for inspecting a semiconductor device or a photo device being an inspecting target.

A seventh aspect is an inspecting method taking a semiconductor device or a photo device as an inspecting target, the method including the steps of: (a) irradiating the inspecting target with pump light; (b) scanning a wide range, which is wider than an irradiated range being irradiated with the pump light in the step (a), with probe light having the same pulse period as the pump light; (c) detecting an electromagnetic wave emitted from the inspecting target in accordance with the irradiation with the probe light in the step (b); and (d) delaying the time of arrival of the probe light at the inspecting target relatively to the pump light.

According to the seventh aspect, even a region not being irradiated with the pump light can be observed in terms of generation, movement, recombination, disappearance and the like of photoexcited carriers by pump-probe measurement. It is thereby possible to perform more detailed inspection on performance or a defect of the semiconductor device or the photo device.

Accordingly, it is an object of the present invention to provide a technique for favorably inspecting a semiconductor device or a photo device by pump-probe measurement.

These and other objects, features, aspects and advantages of the present invention will become more apparent from the following detailed description of the present invention when taken in conjunction with the accompanying drawings.

BRIEF DESCRIPTION OF THE DRAWING

FIG. 1 is a schematic constitutional diagram of an inspecting device according to a preferred embodiment;

FIG. 3 is a plan view showing a state where the surface of a solar cell is scanned with measurement probe light;

FIG. 6 is a conceptual view for explaining generation and movement of photoexcited carriers which occur by irradiation with the measurement pump light;

FIG. 10 is a diagram showing fluctuations in electric field intensity depending on a reverse bias voltage;

FIGS. 14 to 17 are schematic diagrams each showing an inspecting device according to a modified example.

DESCRIPTION OF THE PREFERRED EMBODIMENTS

Figure 2:
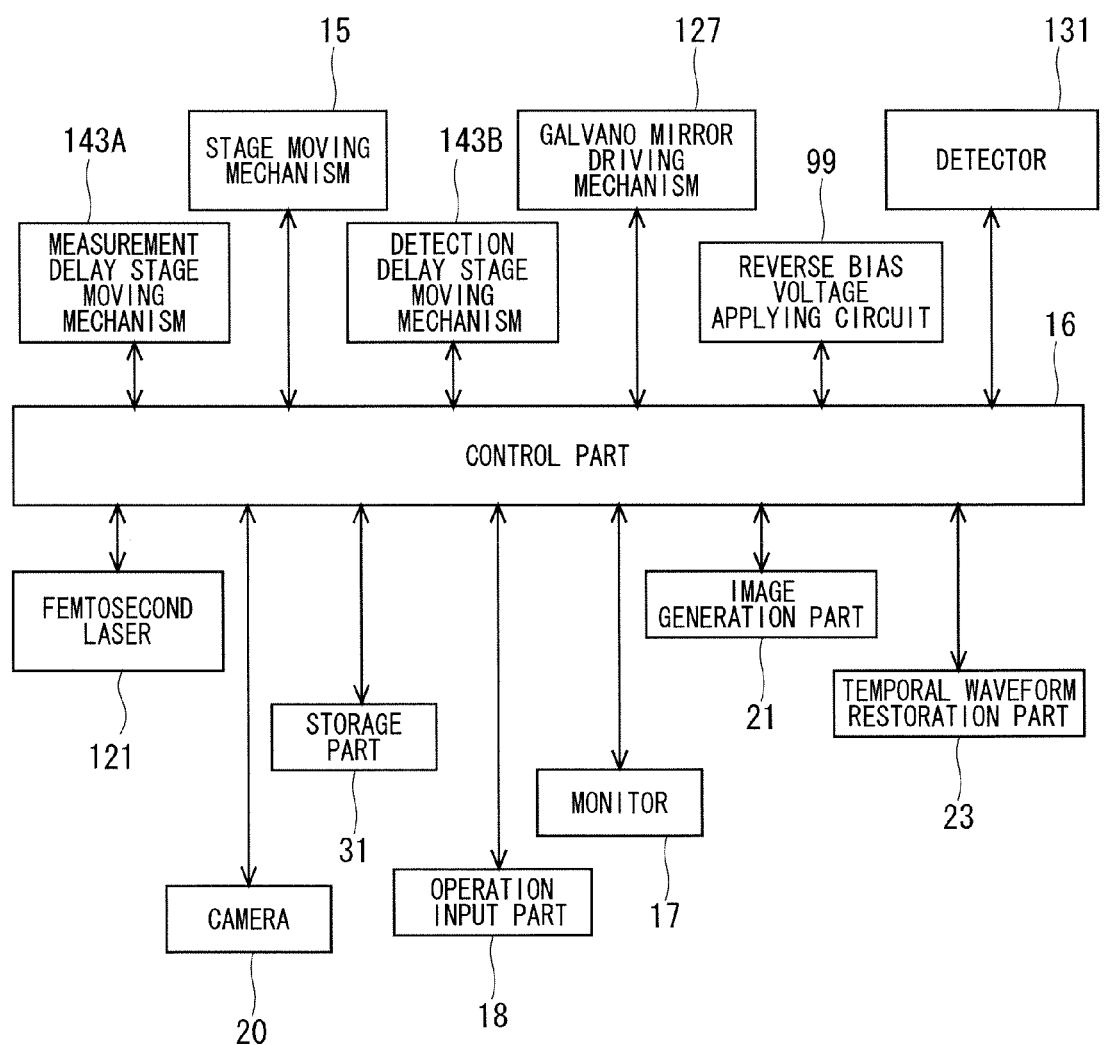
FIG. 2 is a block diagram showing the connecting relations between a control part and other elements.

Hereinafter, a preferred embodiment of the present invention will be described with reference to the accompanying drawings. In the drawings, dimensions or the number of respective parts may be shown as being exaggerated or simplified according to the need in order to facilitate understanding.

<1. Preferred Embodiment>
<1. 1 Configuration and Function>

FIG. 1 is a schematic constitutional diagram of an inspecting device 100 according to an embodiment. The inspecting device 100 irradiates an inspecting target being a semiconductor device or a photo device with pulsed light, and detects an electromagnetic wave (e.g., a terahertz wave with a frequency of 0.1 to 10 THz) emitted from the inspecting target in accordance with the irradiation with the pulsed light, to inspect the inspecting target.

In the present specification, the semiconductor device means an electronic device configured of a semiconductor, such as a transistor, an integrated circuit (IC or LSI), a resistor or a capacitor. Further, the photo device means an electronic device that utilizes a photoelectric effect of a semiconductor, such as a photodiode, an image sensor like a CMOS sensor or a CCD sensor, a solar cell, an LED or the like. Hereinafter, the inspecting target will be specifically described by taking as an example a case where the inspecting target is a flat solar cell 9 being a kind of photo device. A surface 9S of the solar cell 9 may be formed in a flat shape, or may also be formed in a curved shape or the like.

As shown in FIG. 1, the inspecting device 100 includes a stage 11, an irradiation part 12, a detection part 13, a measurement delay part 14A, a detection delay part 14B, a stage moving mechanism 15, and a control part 16.

The solar cell 9 is fixed onto the stage 11 by fixing means, not shown, and held thereon. Examples of the fixing means may include means utilizing an interposing tool for interposing the solar cell 9, an adhesive sheet, and an adsorption hole formed on the surface of the stage 11. However, fixing means other than these may be adopted so long as it can hold the solar cell 9.

The irradiation part 12 is provided with a femtosecond laser 121 as a light source for emitting pulsed light. The femtosecond laser 121 emits pulsed light (pulsed light LP1) with a wavelength that includes a visible light region of not smaller than 300 nm (nanometers) and not larger than 1.5 μm (micrometer), for example. As a preferable example, pulsed light is emitted from the femtosecond laser, the light being linear polarized light with a center wavelength in the vicinity of 800 nm, a cycle of several kHz to several hundred MHz and a pulse width of approximately 10 to 150 femtoseconds. As a matter of course, pulsed light with another wavelength range (visible light wavelength such as a blue wavelength (450 to 495 nm) or a green wavelength (495 to 570 nm)) may be emitted.

The pulsed light LP1 emitted from the femtosecond laser 121 is divided into two parts by means of a half mirror HM1. The one divided pulsed light (measurement pulsed light LP10) is guided to the solar cell 9. A light intensity of the measurement pulsed light LP10 is set to approximately several hundred mW, for example. Further, the other pulsed light (detection pulsed light LP21) is guided to a detector 131 of the detection part 13 for detecting an electromagnetic wave. A light intensity of the detection pulsed light LP21 is set to approximately 5 mW, for example.

The measurement pulsed light LP10 is divided into two parts by means of a half mirror HM2. The one divided measurement pulsed light is modulated by an optical chopper 123 at several kHz (e.g., 2 or 4 kHz). It is to be noted that as the modulation element, an AOM (Acousto-Optic Modulator) or the like may be used. The measurement pulsed light modulated by the optical chopper 123 is guided as measurement probe light LP11 to the surface of the solar cell 9 through a galvano mirror 125.

The galvano mirror 125 changes an optical path of the measurement probe light LP11 to scan the inside of an inspection range, previously set in the solar cell 9, with the measurement probe light LP11. The galvano mirror 125 is driven by a galvano mirror driving mechanism 127. The solar cell 9 is irradiated with the measurement probe light LP11 by the galvano mirror 125 while being scanned thereby in two directions vertical to an optical axis of the measurement probe light LP11. The galvano mirror 125 and the galvano mirror driving mechanism 127 are examples of the scanning mechanism. It is to be noted that other than the galvano mirror 125, a polygon mirror, a piezo mirror, an acousto-optic device or the like can be used. Further, moving the stage 11 with respect to the measurement pulse light LP11 also enables scanning of the predetermined inspection range with the measurement pulsed light LP11. However, scanning can be efficiently performed by using the galvano mirror 125.

The other measurement pulsed light divided by the half mirror HM2 is also guided to the surface of the solar cell 9 as measurement pump light LP13. The measurement delay part 14A is provided on an optical path of the measurement pump light LP13 from the half mirror HM2 to the solar cell 9. The measurement delay part 14A continuously changes the time of arrival of the measurement pump light LP13 at the solar cell 9. The measurement delay part 14A is provided with a measurement delay stage 141A and a measurement delay stage moving mechanism 143A.

It is to be noted that in the present preferred embodiment, the light obtained by dividing the measurement pulsed light LP10 emitted from one femtosecond laser 121 are taken as the measurement probe light LP11 and the measurement pump light LP13. For this reason, the pulse periods of the measurement probe light LP11 and the measurement pump light LP13 agree with each other.

The measurement delay stage 141A is provided with a return mirror 10M for returning the measurement pump light LP13 in an incident direction. The measurement delay stage moving mechanism 143A moves the measurement delay stage 141A parallelly along the incident direction of the measurement pump light LP13 based on control of the control part 16. The parallel movement of the measurement delay stage 141A leads to a continuous change in optical path length of the measurement pump light LP13.

When a portion in the solar cell 9 where an internal electric field exists is irradiated with the measurement probe light LP11 having energy beyond a band gap, photoexcited carriers (free electron and free hole) are generated and accelerated by the internal electric field. A pulsed-current is thereby generated, and accordingly, an electromagnetic wave LT1 is generated. The internal electric field is known to be generated in a pn junction part, a Schottky barrier junction part or the like, for example.

The electromagnetic wave LT1 is generated depending on the state (intensity, direction, etc.) of the internal electric field. That is, the electromagnetic wave LT1 is generated depending on a pn bond, a state of wiring connected to the pn bond, and the like. Therefore, detecting the electromagnetic wave LT1 allows investigation of characteristics of the solar cell 9 and inspection such as a defect judgment.

The measurement delay stage 141A is a device for changing the time difference between the time of arrival of the measurement probe light LP11 at the solar cell 9 and the time of arrival of the measurement pump light LP13 at the solar cell 9. In the present preferred embodiment, a difference in time from excitement of the solar cell 9 by the measurement pump light LP13 to excitement of the solar cell 9 by the measurement probe light LP11 is taken as delay time, and a signal (electromagnetic wave LT1) obtained by the measurement probe light LP11 is measured as a function of the delay time. Thereby, an ultrafast response of the solar cell 9 to optical excitation is measured at a temporal resolution with a high femtosecond region (pump-probe method).

It is to be noted that the time of arrival of the measurement pump light LP13 at the solar cell 9 can be changed by a configuration different from that of the measurement delay stage 141A. Specifically, utilizing an electro-optical effect is considered. In other words, an electro-optic element having a refractive index which changes by changing an applied voltage may be used as a delay element. For example, an electro-optic element disclosed in Japanese Patent Application Laid-Open No. 2009-175127 can be utilized.

Further, it is considered that an optical path length of the measurement probe light LP11 may be changed in place of changing the optical path length of the measurement pump light LP13. Also in this case, the time of arrival of the measurement probe light LP11 at the detector 131 can be delayed relatively to the measurement pump light LP13.

In addition, as described later, the solar cell 9 may be irradiated only with the measurement pump light LP13 and the electromagnetic wave LT1 radiated thereby may be measured. In this case, the measurement pump light LP13 is modulated by a similar modulation device to the optical chopper 123 although it is not shown.

The electromagnetic wave LT1 emitted from the solar cell 9 is collected in parabolic mirrors M1, M2. More specifically, the parabolic mirrors M1, M2 collect the electromagnetic wave LT1 emitted on the same side as the surface 9S that is irradiated with the measurement probe light LP11. Then, the collected electromagnetic wave LT1 is incident on the detector 131.

The detector 131 is configured of a photoconductive switch, on which the detection pulsed light LP21 is incident. The detection pulsed light LP21 is modulated by an optical chopper 145 at several kHz. When the detector 131 is irradiated with the detection pulsed light LP21 in a state where the electromagnetic wave LT1 is incident on the detector 131, a current in accordance with an electric field intensity of the electromagnetic wave LT1 is instantaneously generated in the photoconductive switch. The current in accordance with the electric field intensity is converted into a digital amount as appropriate through a lock-in amplifier, an A/D conversion circuit or the like which is not shown. As thus described, the detection part 13 detects the electric field intensity of the electromagnetic wave LT1 emitted from the solar cell 9 in accordance with the irradiation with the detection pulsed light LP21. It is to be noted that applying another element, such as a nonlinear optical crystal, to the detector 131 can also be considered.

The detection delay part 14B is provided on an optical path of the detection pulsed light LP21 from the half mirror HM1 to the detector 131. The detection delay part 14B changes the time of arrival of the detection pulsed light LP21 at the detector 131. The detection delay part 14B is provided with a detection delay stage 141B and a detection delay stage moving mechanism 143B.

The detection delay stage 141B is provided with a return mirror 10M for returning the detection pulsed light LP21 in an incident direction. The detection delay stage moving mechanism 143B moves the detection delay stage 141B parallelly along the incident direction of the detection pulsed light LP21 based on control of the control part 16. The parallel movement of the delay stage for detection 141B leads to a continuous change in optical path length of the detection pulsed light LP21.

The detection delay stage 141B changes the time difference between the time of arrival of the electromagnetic wave LT1 at the detector 131 and the time of arrival of the detection pulsed light LP21 at the detector 131. In other words, changing the optical path length of the detection pulsed light LP21 by the detection delay stage 141B delays the timing (detection timing or sampling timing) for detecting the electric field intensity of the electromagnetic wave LT1 in the detector 131.

It is considered that the detection delay stage 141B also utilizes the electro-optical effect as does the measurement delay stage 141A. Further, the optical path length of the measurement probe light LP11 or the optical path length of the electromagnetic wave LT1 emitted from the solar cell 9 may be changed in place of changing the optical path length of the detection pulsed light LP21. In any case, the time of arrival of the electromagnetic wave LT1 at the detector 131 can be delayed relatively to the time of arrival of the detection pulsed light LP21 at the detector 131. That is, it is possible to delay the detection timing for the electric field intensity of the electromagnetic wave LT1 in the detector 131.

Further, the inspecting device 100 includes a reverse bias voltage applying circuit 99 for applying a reverse bias voltage to the solar cell 9 at the time of inspection. The reverse bias voltage applying circuit 99 is connected to electrodes (front electrode and back electrode) respectively formed on the light receiving surface of the solar cell 9 and the opposite-side surface thereto, and a reverse bias voltage is applied. A magnitude of a voltage that is applied to the solar cell 9 by the reverse bias voltage applying circuit 99 can be changed based on control from the control part 16.

Applying the reverse bias voltage can increase a depletion layer of the pn junction part. Hence it is possible to increase the electric field intensity of the electromagnetic wave LT1 detected in the detector 131, so as to improve detection sensitivity of the electromagnetic wave LT1 in the detection part 13. However, it is also possible to omit the reverse bias voltage applying circuit 99.

The stage moving mechanism 15 is a device for moving the stage 11 in a two-dimensional plane and is configured of an X-Y table or the like, for example. The stage moving mechanism 15 moves the solar cell 9 held on the stage 11 relatively to the irradiation part 12. The inspecting device 100 can move the solar cell 9 to an arbitrary position in the two dimensional plane by means of the stage moving mechanism 15. The stage moving mechanism 15 is an example of the irradiated position changing part.

FIG. 2 is a block diagram showing the connecting relations between the control part 16 and other elements. The control part 16 is configured of a general computer or the like, provided with a CPU, a ROM, a RAM and the like which are not shown. As shown in FIG. 2, the control part 16 is connected to the femtosecond laser 121, the detector 131, the measurement delay stage moving mechanism 143A, the detection delay stage moving mechanism 143B, the stage moving mechanism 15, the galvano mirror driving mechanism 127 and the reverse bias voltage applying circuit 99. The control part 16 controls an operation of each of these elements or receives data from each of these elements.

Further, the control part 16 is connected to an image generation part 21 and a temporal waveform restoration part 23. The image generation part 21 and the temporal waveform restoration part 23 are functions realized by the CPU provided in the control part 16, but those may be realized on a hardware basis by means of a dedicated circuit.

In the inspection range of the solar cell 9 (part or the whole of the solar cell 9), the image generation part 21 generates an electric field intensity distribution image formed by visualizing distribution of the electric field intensity of the electromagnetic wave LT1 emitted by the irradiation with the pulsed light LP11. In the electric field intensity distribution image, a difference in electric field intensity is visually expressed by different colors, different patterns or the like, for example.

The temporal waveform restoration part 23 restores a temporal waveform of the electromagnetic wave LT1 emitted from the solar cell 9 based on the electric field intensity detected by the detector 131. Specifically, by moving the detection delay stage 141B, the time of arrival of the detection pulsed light LP21 at the detector 131 is changed, to acquire the electric field intensity of the electromagnetic wave LT1 detected in each phase. Then, the acquired electric field intensity is plotted on a temporal axis, to restore the temporal waveform of the electromagnetic wave LT1.

The control part 16 is connected with a storage part 31 for storing a variety of data. The storage part 31 may be configured of a portable media (e.g., magnetic media, optical disk media, semiconductor memory, etc.), a main storage memory or the like other than a fixed disk such as a hard disk. Further, the control part 16 may be connected with the storage part 31 through a network line.

The control part 16 is connected with a monitor 17 and an operation input part 18. The monitor 17 is a display device such as a liquid crystal display, and displays a variety of image information to an operator. The monitor 17 displays an image of the surface 9S of the solar cell 9, photographed by a camera 20 or the like, the electric field intensity distribution image generated by the image generation part 21, the temporal waveform of the electromagnetic wave LT1 restored by the temporal waveform restoration part 23, and the like. Further, the monitor 17 displays a GUI (Graphical User Interface) screen which is necessary for setting an inspection condition. Examples of the inspection condition may include an inspection range and positions to which the measurement delay stage 141A and the detection delay stage 141B are fixed.

The camera 20 can be utilized for specifying positions irradiated with the measurement probe light LP11 and the measurement pump light LP13.

The operation input part 18 is configured of a variety of input devices such as a mouse and a keyboard. The operator can perform a predetermined operation input through the operation input part 18. It is to be noted that the monitor 17 may be configured as a touch panel, thereby to function as the operation input part 18.

<Scanning with Measurement Probe Light>

FIG. 3 is a plan view showing a state where the surface 9S of the solar cell 9 is scanned with the measurement probe light LP11. As shown in FIG. 3, the surface of the solar cell 9 is provided with a busbar electrode part 91 extending in a vertical direction (y-axis direction) and a plurality of thin finger electrode parts 93 extending in a lateral direction (x-axis direction) from the busbar electrode part 91. These busbar electrode part 91 and finger electrode parts 93 constitute part of the front electrode.

As shown in FIG. 3, in the pump-probe measurement, a predetermined range is irradiated with the measurement pump light LP13 in a spot-like shape. A range (probe light spot SP11) irradiated with the measurement probe light LP11 itself is smaller than a range (pump light spot SP13) irradiated with the measurement pump light LP13 (e.g., approximately 1/10 as large at the maximum). However, the range scanned with the measurement probe light LP11 by means of the galvano mirror 125 is a wider range (wide range R11) than the range irradiated with the measurement pump light LP13.

As a specific aspect of the scanning, it is considered that the inside of the wide range R11 is scanned while the probe light spot SP11 of the measurement probe light LP11 is reciprocated from side to side along the x-axis direction, as shown in FIG. 3. As a matter of course, the probe light spot SP11 may be moved in one direction along the x-axis direction and then returned to the original position, and thereafter moved to a next stage in the y-axis direction and moved in the same direction as previous. Further, the probe light spot SP11 may be moved along the y-axis direction instead of the x-axis direction.

<Pump-Probe Measurement>

Figure 4:
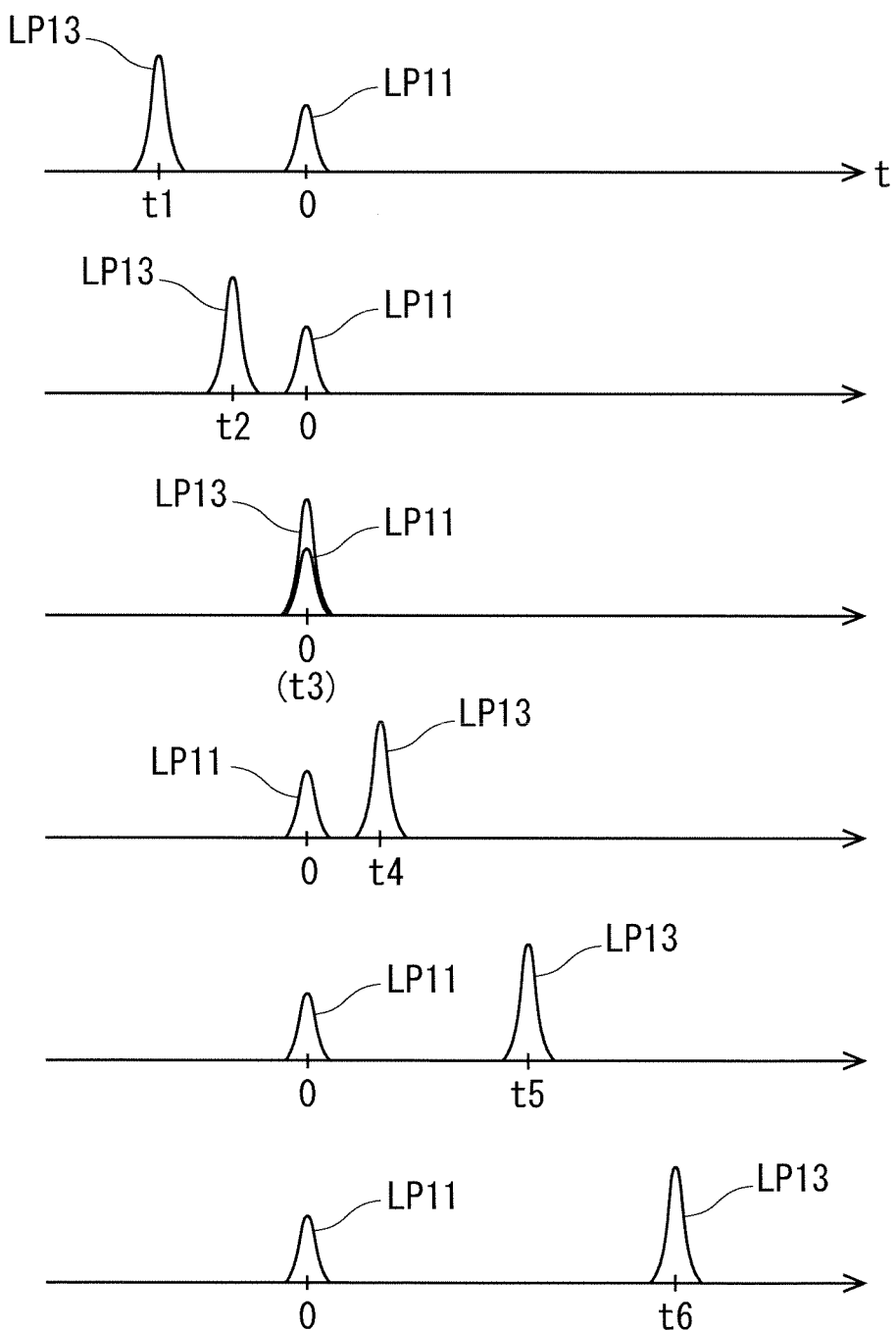
FIG. 4 is a diagram showing the temporal relation between the measurement probe light and measurement pump light.

Next, the pump-probe measurement will be described. FIG. 4 is a diagram showing the temporal relation between the measurement probe light LP11 and the measurement pump light LP13. In FIG. 4, a lateral axis indicates the time. As described above, the measurement pump light LP13 can be delayed by the measurement delay part 14A with respect to the measurement probe light LP11. FIG. 4 shows the measurement probe light LP11 and the measurement pump light LP13 at the time when the delay time is changed respectively to t1 to t6, sequentially from the above.

When the delay time is t1, t2, the measurement probe light LP11 arrives at the solar cell 9 earlier than the measurement pump light LP13. That is, irradiation is performed with the measurement probe light LP11 before the photoexcited carriers are generated by the measurement pump light LP13. Further, when the delay time is t3, the measurement probe light LP11 arrives at the solar cell 9 simultaneously with the measurement pump light LP13. That is, this is the state of there being no phase difference between the measurement probe light LP11 and the measurement pump light LP13. Moreover, when the delay time is t4, t5, and t6, the measurement probe light LP11 arrives at the solar cell 9 later than the measurement pump light LP13. That is, irradiation is performed with the measurement probe light LP11 after the photoexcited carriers have been generated by the measurement pump light LP13.

Figure 5:
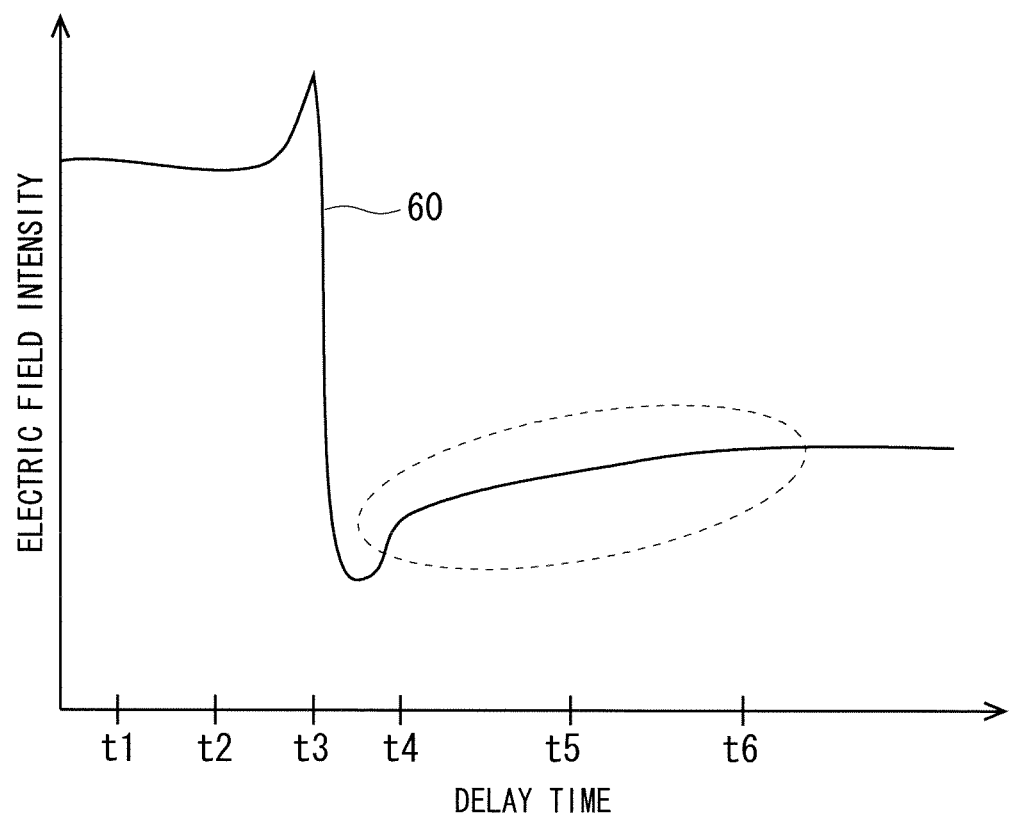
FIG. 5 is a diagram showing a waveform of an electric field intensity of an electromagnetic wave which is emitted when the delay time between the measurement probe light and the measurement pump light is changed.

FIG. 5 is a diagram showing a waveform 60 of an electric field intensity of an electromagnetic wave which is emitted when the delay time between the measurement probe light LP11 and the measurement pump light LP13 is changed. In FIG. 5, a lateral axis indicates the delay time, and a vertical axis indicates the electric field intensity. In the pump-probe measurement, typically, the electric field intensity of the emitted electromagnetic wave almost becomes maximal when the delay time is "0" (namely at t3). However, when the delay time becomes larger than that in a positive direction (namely when the measurement probe light LP11 is further delayed with respect to the measurement pump light LP13), the electric field intensity abruptly decreases. Further, at t4, t5 and t6 when the delay time becomes larger in the positive direction, the electric field intensity gradually becomes larger by degrees (portion surrounded by a dotted line in FIG. 5). The inclination of the electric field intensity from t4 to t6 corresponds to the time when electrons excited by the measurement pump light LP13 are alleviated (recombined).

FIG. 6 is a conceptual view for explaining generation and movement of photoexcited carriers which occur by irradiation with the measurement pump light LP13. As shown in FIG. 6, in the solar cell 9, an n-type semiconductor layer 94 and a p-type semiconductor layer 95 are laminated, and a depletion layer 96 is formed in a junction part (pn junction part) of the n-type semiconductor layer 94 and the p-type semiconductor layer 95. Further, the finger electrode part 93 as part of the front electrode is formed on the upper surface of the n-type semiconductor layer 94, and a back electrode 97 is formed on the lower surface of the p-type semiconductor layer 95.

As shown in FIG. 6, when irradiation is performed with the measurement pump light LP13, photoexcited carriers (free electron 41 and hole 43) are generated in the depletion layer 96 (time T11). Being influenced by diffusion, the internal electric field or the external electric field, the generated free electrons 41 move as majority carriers in the n-type semiconductor layer 94 toward the front electrode (finger electrode part 93) (time T12 to T15).

The hole 43 also moves in the p-type semiconductor layer. However, the moving speed of the hole 43 tends to be slow as compared to that of the free electron 41. For this reason, in the pump-probe measurement which is an analysis on the subpicosecond order, movement of the free electron 41 is mainly analyzed.

Figure 7:
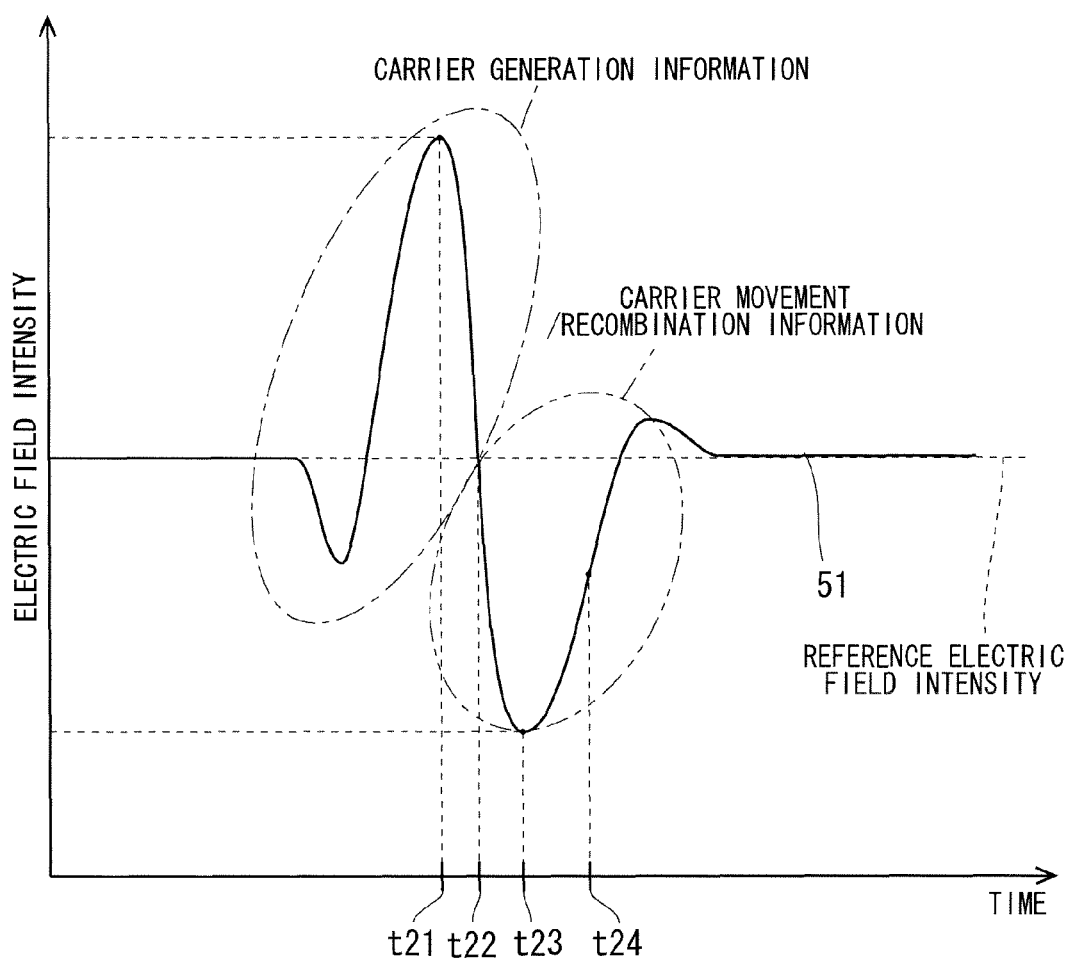
FIG. 7 is a diagram showing a temporal waveform of an electromagnetic wave emitted from the solar cell by irradiation with the measurement probe light.

FIG. 7 is a diagram showing a temporal waveform 51 of the electromagnetic wave LT1 emitted from the solar cell 9 by irradiation with the measurement probe light LP11. In FIG. 7, a lateral axis indicates the time, and a vertical axis indicates the electric field intensity. It is to be noted that the temporal waveform 51 shown in FIG. 7 is one restored based on the electric field intensity of the electromagnetic wave LT1 detected in a large number of detection timing followed by irradiation of the same one area on the solar cell 9 with the measurement probe light LP11 in the state of no irradiation with the measurement pump light LP13 and by driving of the detection delay part 14B.

A larger electric field intensity than an electric field intensity (reference electric field intensity) in a normal state is set to be a positive electric field intensity, and a smaller electric field intensity than the reference electric field intensity is set to be a negative electric field intensity. The temporal waveform 51 takes a positive peak at time t21, subsequently has the reference electric field intensity at time t22, and thereafter takes a negative peak at time t23. Then, the electric field intensity of the temporal waveform 51 again comes closer to the reference electric field intensity after time t23 (e.g., at time t24).

In the temporal waveform 51, a signal of the electric field intensity that changes on the positive side (portion surrounded by an alternate long and short dash line) is considered as mainly including information (carrier generation information) of the time when the photoexcited carriers are generated by the irradiation with the measurement probe light LP11. Further, in the temporal waveform 51, a signal of the electric field intensity that changes on the negative side (portion surrounded by an alternate long and two short dashes line) is considered as mainly including information (carrier movement/recombination information) of movement and recombination of the photoexcited carriers generated by the irradiation with the measurement probe light LP11. Therefore, the detection delay part 14B is driven such that the time for driving matches the time t22 to t24, whereby it is possible to acquire the information of generation, movement and recombination of the photoexcited carriers in accordance with the irradiation with the measurement probe light LP11.

<1.2 Inspection>

Next, a flow for inspection of the solar cell 9 in the inspecting device 100 will be described. As described above, in the inspecting device 100, the solar cell 9 is inspected by performing the pump-probe measurement. Before the inspection by the pump-probe measurement, setting for a variety of conditions (initial setting) is performed.

Figure 8:
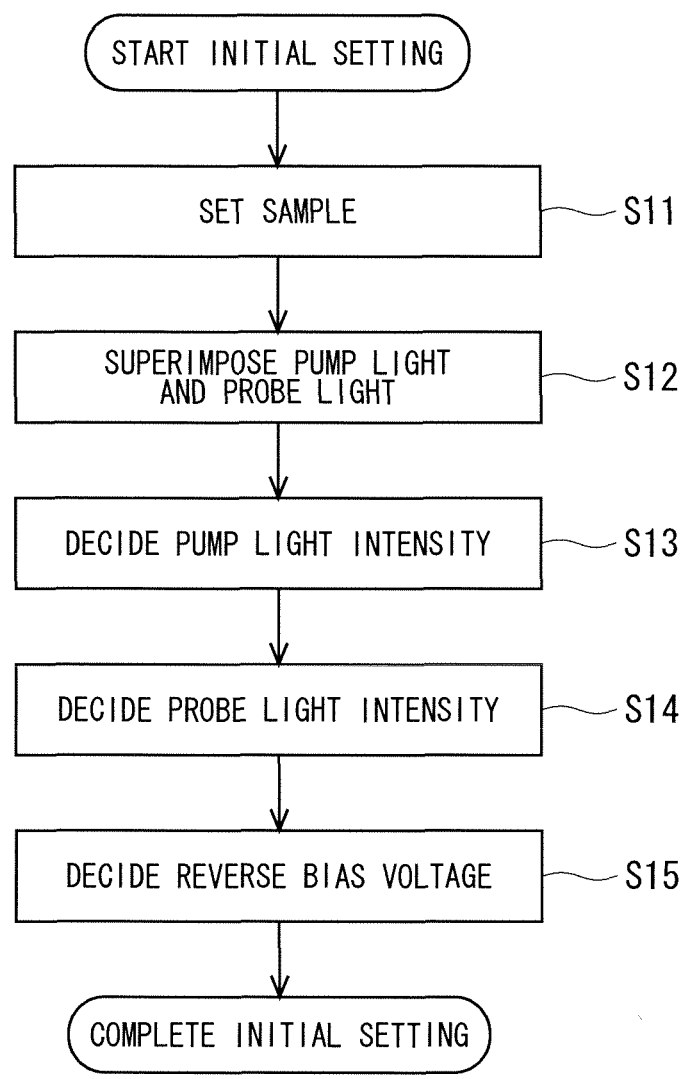
FIG. 8 is a flowchart showing an example of initial setting.

FIG. 8 is a flowchart showing an example of the initial setting. In this initial setting, first, the solar cell 9 being a sample is set on the stage 11 (FIG. 8: step S11). Then, the measurement pump light LP13 and the measurement probe light LP11 are superimposed (FIG. 8: step S12). Specifically, in step S12, the galvano mirror 125 is adjusted such that the probe light spot SP11 of the measurement probe light LP11 is within the pump light spot SP13 of the measurement pump light LP13.

When the measurement probe light LP11 is superimposed on the measurement pump light LP13, the light intensity of the measurement pump light LP13 is decided (FIG. 8: step S13), the light intensity of the measurement probe light LP11 is decided (FIG. 8: step S14), and the magnitude of the reverse bias voltage is decided (FIG. 8: step S15). It is to be noted that steps S13 to S15 are not necessarily executed in this order.

Figure 9:
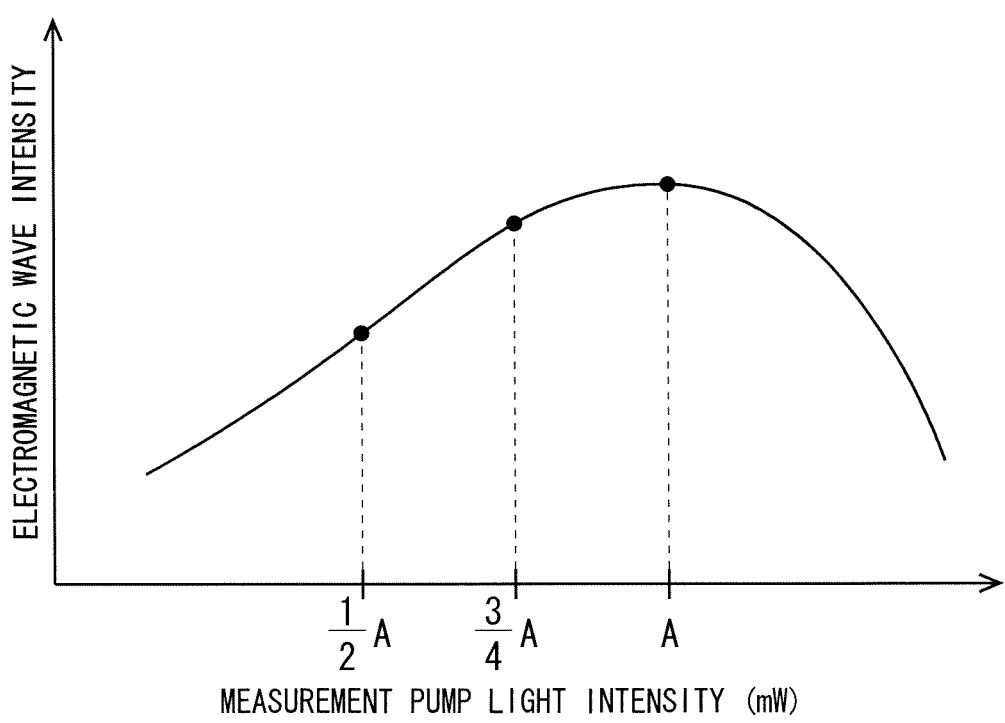
FIG. 9 is a diagram showing the relation between a light intensity of the measurement pump light and an electric field intensity of the emitted electromagnetic wave.

First, the decision of the light intensity of the measurement pump light LP13 (step S13) will be described. FIG. 9 is a diagram showing the relation between the light intensity of the measurement pump light LP13 and the electric field intensity of the emitted electromagnetic wave. In FIG. 9, a lateral axis indicates the light intensity, and a vertical axis indicates the electric field intensity.

As shown in FIG. 9, when the light intensity of the measurement pump light LP13 is increased, the electric field intensity becomes maximal at a certain point of the light intensity. Hereinafter, this light intensity is taken as "A". Then, even when the light intensity is made larger than A, there occurs a phenomenon that the electric field intensity is weakened. This is considered due to that the light is so strong as to cause generation of a large amount of photoexcited carriers and they remain without moving to the electrodes. Then in executing the pump-probe measurement, the light intensity of the measurement pump light LP13 is set so as to be preferably smaller than the light intensity at the time when the maximum electric field intensity is detected (the light intensity at maximum electric field), and more preferably within the range of ½ to ¾ of the light intensity at maximum electric field. By setting the light intensity of the measurement pump light LP13 in such a range, highly reliable data can be obtained.

Further, the light intensity of the measurement probe light LP11 to be decided in step S14 is decided such that an S/N of the intensity of the detected electromagnetic wave is held high while it is as small a light intensity as possible.

Subsequently, the decision of the magnitude of the reverse bias voltage (step S15) will be described. FIG. 10 is a diagram showing fluctuations in electric field intensity depending on the reverse bias voltage. In the present preferred embodiment, the pump-probe measurement is executed by applying different reverse bias voltages, to decide the reverse bias voltage. Waveforms 61 to 64 shown in FIG. 10 correspond to ones obtained when the reverse bias voltages are set at 0.5 V, 1 V, 3 V and 5 V, respectively. In FIG. 10, a lateral axis indicates the delay time between the measurement probe light LP11 and the measurement pump light LP13, and a vertical axis indicates the electric field intensity.

As shown in FIG. 10, the larger the reverse bias voltage to be applied to the solar cell 9 is made, the more the S/N ratio of the electric field intensity of the emitted electromagnetic wave LT1 improves. However, with a strong external electric field being generated in the solar cell 9, there occurs a problem of deterioration in detection sensitivity of dynamics of the photoexcited carriers generated by the measurement probe light LP11. Therefore, the minimum voltage is selected out of the reverse bias voltages each having a typical waveform obtained by the pump-probe measurement. The typical waveform is a waveform that the electric field intensity significantly weakens when the delay time between the measurement probe light LP11 and the measurement pump light LP13 exceeds 0, and an alleviation time smoothly changes, as the waveform 60 shown in FIG. 5, for example. In the example shown in FIG. 10, the waveforms 62 to 64 are typical waveforms in the pump-probe measurement. For this reason, out of the plurality of reverse bias voltages (1 V, 3 V, and 5 V) corresponding to these waveforms 62 to 64, 1 V being the minimum voltage is selected as the reverse bias voltage.

Deciding the magnitude of the reverse bias voltage as thus described can lead to selection of a reverse bias voltage having so a suitable magnitude as not to hinder the pump-probe measurement. Hence it is possible to favorably observe dynamics of the photoexcited carriers generated by the measurement probe light LP11, while improving the S/N ratio of the detected electric field intensity.

Figure 11:
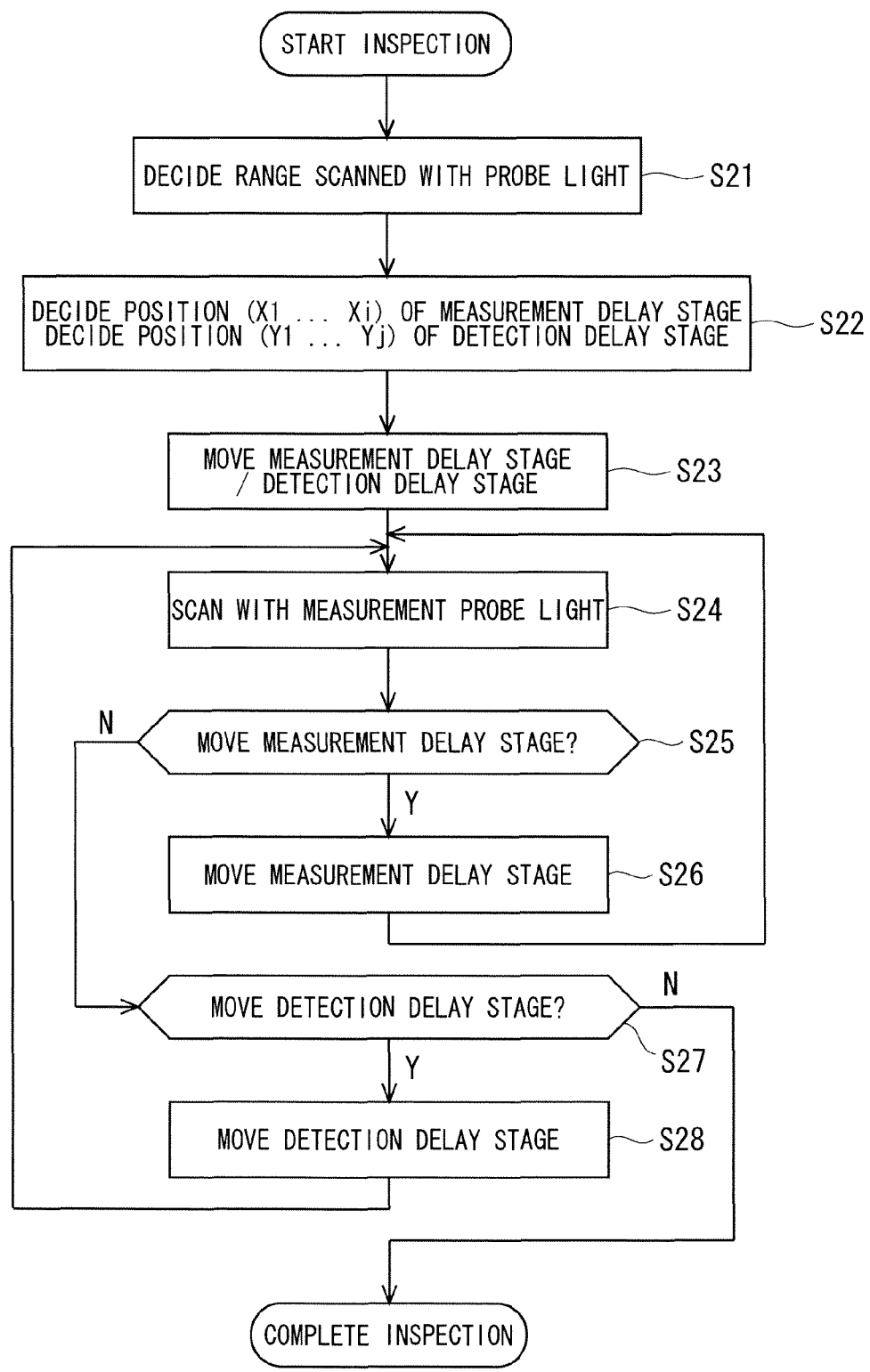
FIG. 11 is a flowchart showing an example of inspection.

When the initial setting is completed, the inspection of the solar cell 9 is started. FIG. 11 is a flowchart showing an example of inspection. In the following description, it is assumed that each operation of the inspecting device 100 is controlled by the control part 16 unless otherwise mentioned. Further, depending on the contents of steps, a plurality of steps may be executed in parallel or the order for executing each step may be changed as appropriate.

First, as for the solar cell 9, a range to be inspected (inspection range) is set (FIG. 11: step S21). This setting process is executed by the operator inputting coordinate information corresponding to a desired inspection range into the control part 16 through the operation input part 18. Thereby, the position irradiated with the measurement pump light LP13 and the range scanned with the measurement probe light LP11 (wide range R11) are set as shown in FIG. 3.

When the inspection range is set, positions to be arranged with the measurement delay stage 141A and the detection delay stage 141B at the time of the pump-probe measurement are decided (FIG. 11: step S22). Deciding a plurality of positions (X1 . . . Xi) to be arranged with the measurement delay stage 141A during the pump-probe measurement leads to setting for a plurality of delay time when the probe light for measurement LP11 is delayed with respect to the pump light for measurement LP13. Further, deciding a plurality of positions (Y1 . . . Yj) to be arranged with the delay stage for detection 141B during the pump-probe measurement leads to setting for a plurality of delay time when the pulsed light for detection LP21 is delayed with respect to the emitted electromagnetic wave LT1.

The measurement delay stage 141A and the detection delay stage 141B are moved to the positions set in step S22 (e.g., positions X1, Y1) (FIG. 11: step S23). Then, scanning with the measurement probe light LP11 is performed in a state where irradiation with the measurement pump light LP13 is performed (FIG. 11: step S24). The scanning with the measurement probe light LP11 is performed as described in FIG. 3. That is, the wide range R11 which is wider than the range (pump light spot SP13) irradiated with the measurement pump light LP13 is scanned with the measurement probe light LP11. Then, information of the electric field intensity of the electromagnetic wave LT1 detected by the detector 131 is stored into the storage part 31 in association with information (positional information) of the position irradiated with the measurement probe light LP11.

Upon completion of the scanning in step S24, it is determined whether or not to move the measurement delay stage 141A (step S25). That is, in step S25, it is determined whether or not the pump-probe measurement has been performed by arranging the measurement delay stage 141A in all of the plurality of positions (X1 . . . Xi) set in step S22.

When the measurement delay stage 141A needs to be moved (YES in step S25), the measurement delay stage 141A is moved (FIG. 11: step S26). In this step S26, the measurement delay stage 141A is arranged in the position where it has not been arranged out of the plurality of positions (X1 . . . Xi). Then, the process returns to step S24, and the scanning with the measurement probe light LP11 is performed. When the measurement delay stage 141A does not need to be moved (NO in step S25), the next step S27 is executed.

In step S27, it is determined whether or not to move the detection delay stage 141B. That is, in step S27, it is determined whether or not the pump-probe measurement has been performed by arranging the detection delay stage 141B in all of the plurality of positions (Y1 . . . Yj) set in step S22.

When the detection delay stage 141B needs to be moved (YES in step S27), the detection delay stage 141B is moved (FIG. 11: step S28). In this step S28, the detection delay stage 141B is arranged in the position where it has not been arranged out of the plurality of positions (Y1 . . . Yj). When it does not need to be moved (NO in step S27), the inspection by the pump-probe measurement is completed.

It is to be noted that the position that is arranged with the detection delay stage 141B may be restricted to one position. That is, the pump-probe measurement may be executed while the timing for detecting the electromagnetic wave LT1 by the detector 131 is fixed to one timing. For example, it is considered that the detection delay stage 141B is fixed to a position corresponding to the timing (i.e., time t21) when the electric field intensity of the electromagnetic wave LT1 emitted by the irradiation with the probe light for measurement LP11 becomes maximal, which is shown in FIG. 7.

Figure 12:
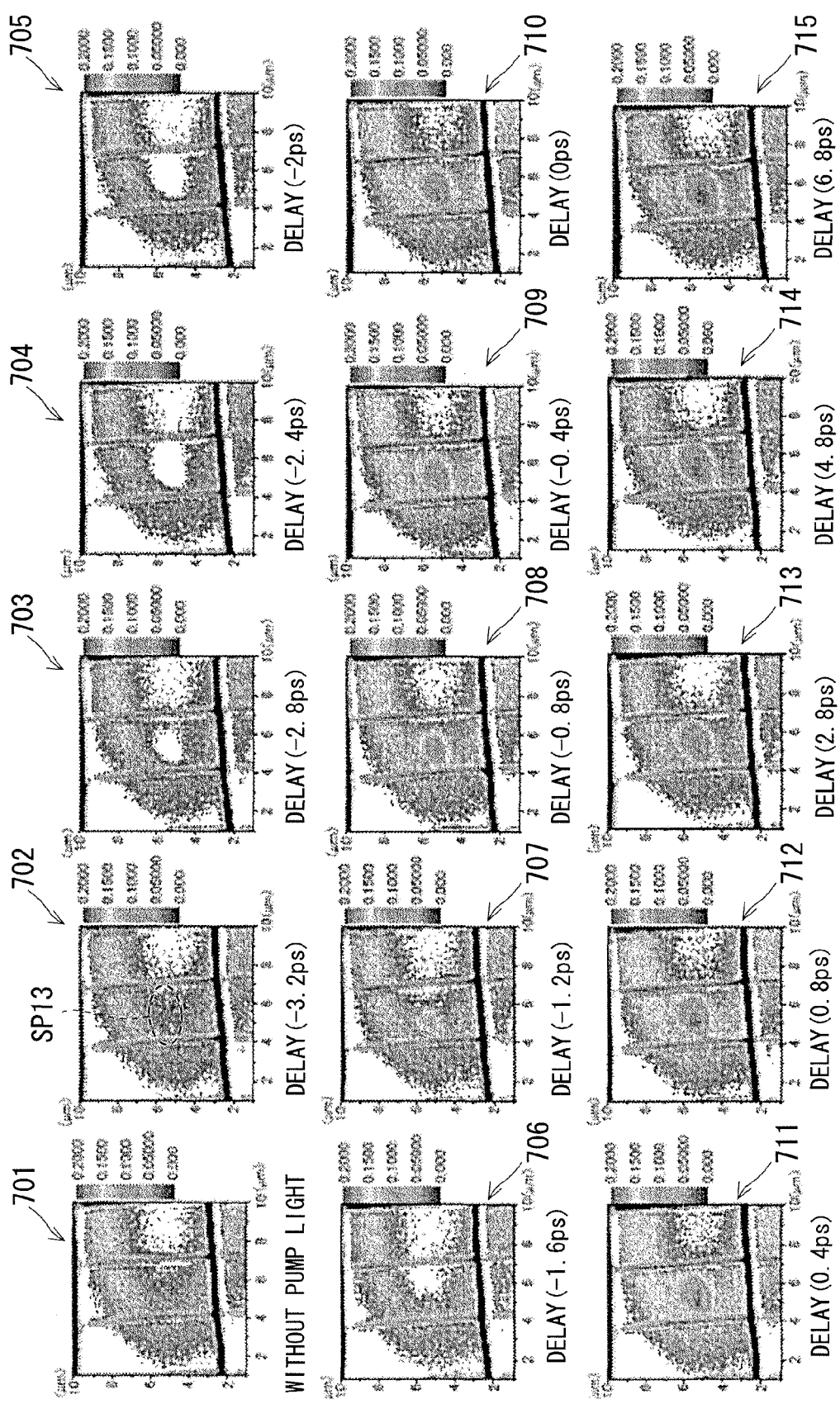
FIG. 12 is a view showing examples of a plurality of electric field intensity distribution images with different delay time.
Figure 13:
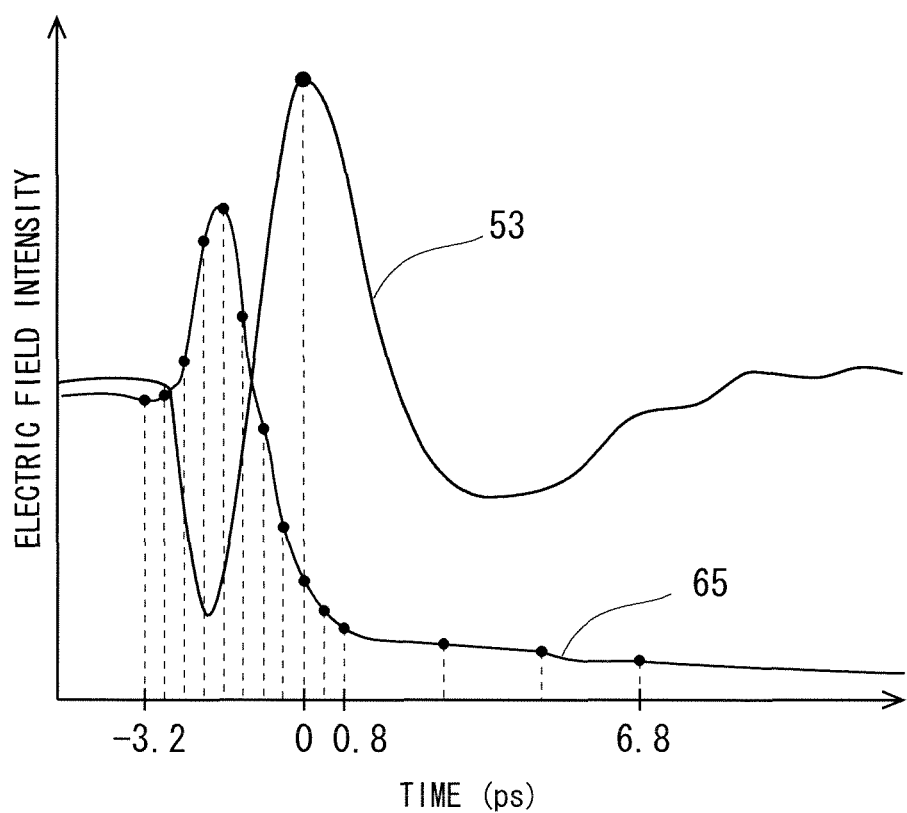
FIG. 13 is a diagram showing a temporal waveform of an electromagnetic wave generated by irradiation only with the measurement pump light, and a waveform obtained by pump-probe measurement.

FIG. 12 is a view showing examples of a plurality of electric field intensity distribution images 701 to 715 with different delay time. Further, FIG. 13 is a diagram showing a temporal waveform 53 of an electromagnetic wave generated by irradiation only with the pump light for measurement LP13, and a waveform 65 obtained by the pump-probe measurement. In FIG. 13, a lateral axis indicates the time, and a vertical axis indicates the electric field intensity.

Each of the plurality of electric field intensity distribution images 701 to 715 shown in FIG. 12 is one obtained in the following manner. First, the inspection range is irradiated only with the measurement pump light LP13, to restore the temporal waveform 53 of the emitted electromagnetic wave. Then, the detection delay stage 141B is fixed to a position corresponding to the detection timing when the electric field intensity in the temporal waveform 53 becomes maximal. Subsequently, the pump-probe measurement is performed by driving the measurement delay stage 141A while performing irradiation with the measurement probe light LP11 such that it is superimposed on the measurement pump light LP13. Accordingly, the waveform 65 shown in FIG. 13 is acquired.

In the waveform 65, the delay time of the measurement probe light LP11 with respect to the measurement pump light LP13 at the time when the temporal waveform 53 becomes the maximum electric field intensity is taken as 0 ps (delay (0 ps)). The electric field intensity distribution images 702 to 715 are ones formed by imaging electric field intensity distribution obtained by fixing the measurement delay stage 141A to positions corresponding respectively to a plurality of delay time (−3.2 ps, −2.8 ps, −2.4 ps, −2.0 ps, −1.6 ps, −1.2 ps, −0.8 ps, −0.4 ps, 0 ps, 0.4 ps, 0.8 ps, 2.8 ps, 4.8 ps, and 6.8 ps) and scanning a predetermined inspection range (wide range R11) with the measurement probe light LP11.

In FIG. 12, the pump light spot SP13 irradiated with the measurement pump light LP13 is shown on the electric field intensity distribution image 702. Further, the electric field intensity distribution image 701 is one formed by imaging electric field intensity distribution obtained by scanning the inspection range with the measurement probe light LP11 without irradiating it with the measurement pump light LP13.

According to the waveform 65 shown in FIG. 13, the range of the abrupt change in electric field intensity is from −3.2 ps to 0.8 ps. Then, in this range, the delay time is finely divided (here, 0.4 ps each), to acquire a large number of electric field intensity distribution images 702 to 712. Hence dynamics of the photoexcited carriers before and after the irradiation with the measurement pump light LP13 (especially the process of generation of the photoexcited carriers) can be analyzed in detail. Further, in the range (0.8 to 6.8 ps) where the change in electric field intensity is gentle in the waveform 65, a change is made such that the delay time is roughly divided (here, per 2.0 pc). As a matter of course, how to divide the delay time is not restricted to such a manner as above, and can be changed as appropriate in accordance with the purpose of the inspection.

As shown in FIG. 12, according to the inspecting device 100 in the present preferred embodiment, a variety of information, such as information of excitement, movement, recombination and disappearance of the photoexcited carriers and a change in electric field by the irradiation with the measurement pump light LP13, can be visually captured by imaging.

Especially in the present preferred embodiment, the wide range which is wider than the range (pump light spot SP13) irradiated with the measurement pump light LP13 is scanned with the measurement probe light LP11. Hence it is possible to obtain information on dynamics of photoexcited carriers out of the range irradiated with the measurement pump light LP13.

<2. Modified Example>

Although the preferred embodiment has been described above, the present invention is not restricted to the foregoing but a variety of modifications can be made.

For example, two femtosecond lasers 121 may be provided, and pulsed light from the one femtosecond laser may be taken as the measurement probe light LP11 while pulsed light from the other femtosecond laser may be taken as the measurement pump light LP13. In this case, synchronizing the two femtosecond lasers 121 can delay the measurement probe light LP11 with respect to the measurement pump light LP13. For this reason, the measurement delay stage 141A can be omitted. Similarly, the measurement probe light LP11 and the detection pulsed light LP21 may be made to be outputted respectively from the two femtosecond lasers. In this case, the detection delay stage 141B can be omitted.

Further, when the inspecting target is a photo device, irradiation may be performed while continuous light is superimposed on the inspection range so as to perform inspection in a state close to the operating state of the photo device. As the continuous light, there can be considered light having a single wavelength or a plurality of wavelength in a light receiving wavelength region suitable for each photo device, white light such as pseudo sunlight, and the like.

Moreover, in the above preferred embodiment, as shown in FIG. 1, the surface 9S of the solar cell 9 is irradiated with the measurement probe light LP11 and the measurement pump light LP13, and the electromagnetic wave LT1 is detected which is emitted on the surface 9S side non-coaxially with the measurement probe light LP11 (non-coaxial reflection type). However, the inspecting device according to the present invention is not restricted to such a configuration, and may have configurations such as inspecting devices 100A to 100D described below.

FIG. 14 is a schematic diagram of the inspecting device 100A according to the modified example. The inspecting device 100A is configured such that the detector 131 detects the electromagnetic wave LT1 emitted coaxially with the measurement probe light LP11 (coaxial reflection type). The inspecting device 100A is provided with a transparent conductive film substrate 133 formed with an ITO film or the like which reflects the electromagnetic wave LT1 while transmitting the measurement probe light LP11 therethrough.

Figure 15:
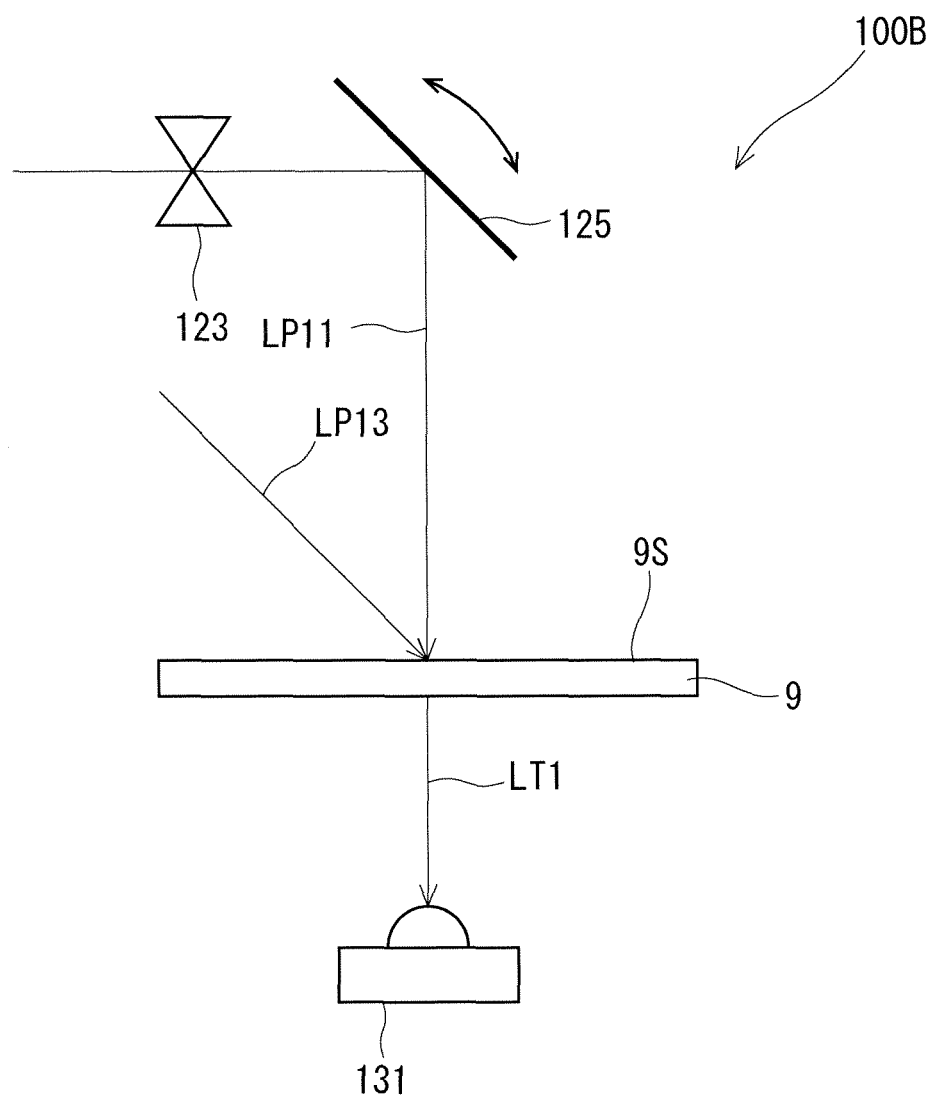

FIG. 15 is a schematic diagram of the inspecting device 100B according to the modified example. The inspecting device 100B is configured such that the detector 131 detects the electromagnetic wave LT1 emitted on the back side opposite to the surface 9S of the solar cell 9 which is irradiated with the measurement probe light LP11 and the like (transmission type).

FIG. 16 is a schematic diagram of the inspecting device 100C according to the modified example. The inspecting device 100C is configured such that the detector 131 detects the electromagnetic wave LT1 emitted on the surface 9S side as in the inspecting device 100A, while irradiation is made so as to make the measurement probe light LP11 coaxial with the measurement pump light LP13 (probe-light/pump-light coaxial reflection type).

Figure 17:
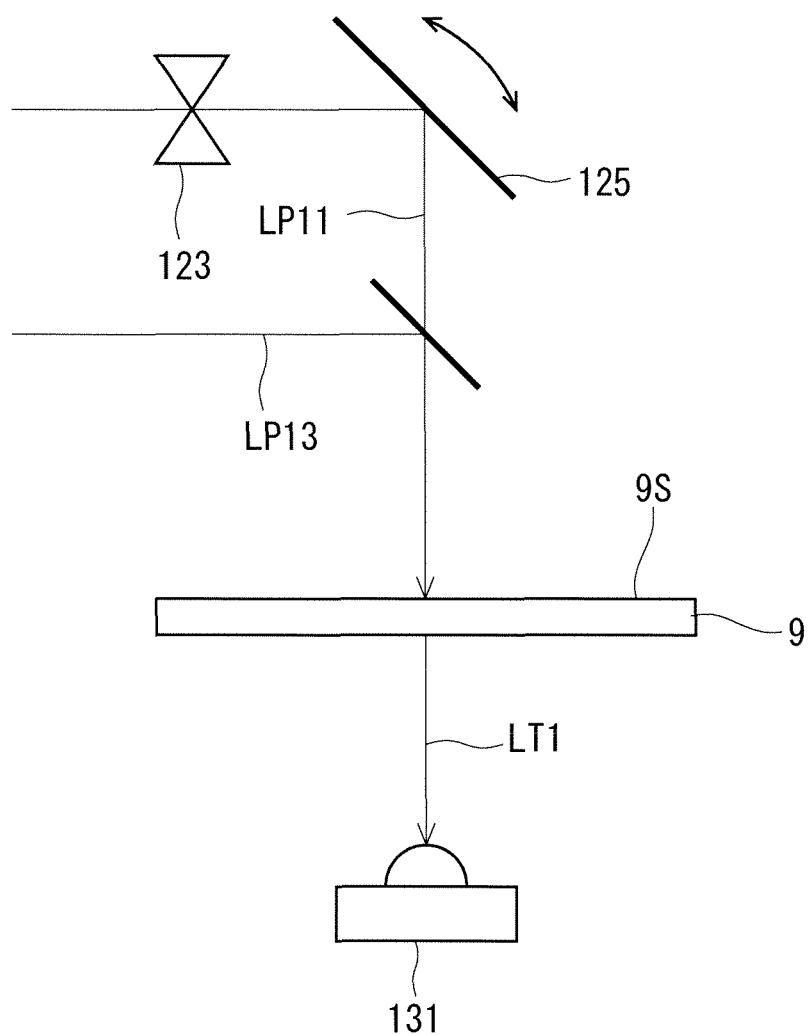

FIG. 17 is a schematic diagram of the inspecting device 100D according to the modified example. The inspecting device 100D is configured such that the detector 131 detects the electromagnetic wave LT1 emitted on the back side of the solar cell 9, while irradiation is performed so as to make the measurement probe light LP11 coaxial with the measurement pump light LP13 as in the inspecting device 100C (probe-light/pump-light coaxial transmission type).

While the invention has been shown and described in detail, the foregoing description is in all aspects illustrative and not restrictive. It is therefore understood that numerous modifications and variations can be devised without departing from the scope of the invention.

What is claimed is:

1. An inspecting device comprising:
   an irradiation part for irradiating an inspecting target with each of pump light and probe light having the same pulse period;
   a detection part for detecting an electromagnetic wave generated from said inspecting target by irradiating said inspecting target with said probe light;
   a measurement delay part for delaying the time of arrival of said probe light at said inspecting target relatively to said pump light; and
   a reverse bias voltage applying part for applying a reverse bias voltage to said inspecting target, wherein
   said irradiation part includes a scanning mechanism to scan with said probe light a scanned and observed area which is larger than an irradiated area being irradiated with said pump light in said inspecting target, an area which is not irradiated with said pump light being also observed in addition to the irradiated area, and
   a diameter of a spot of said probe light is smaller than a diameter of a spot of said pump light, and
   the reverse bias voltage applied by said reverse bias voltage applying part is variable.

2. The inspecting device according to claim 1, further comprising:
   an image generation part for generating an image indicating distribution of an electric field intensity of said electromagnetic wave detected by said detection part.

3. The inspecting device according to claim 2, wherein said measurement delay part gives delay time to said probe light for delaying the time of arrival of said probe light at said inspecting target with respect to said pump light, the delay time being changed at a predetermined time width during inspection of the inspecting target and said predetermined time width being variable.

4. The inspecting device according to claim 1, further comprising:
   an irradiated position changing part for changing a position irradiated with said pump light.

5. The inspecting device according to claim 1, wherein said detection part is provided with a detector for receiving detection pulsed light having the same pulse period as said probe light, to detect an electromagnetic wave generated in accordance with the irradiation with said probe light, and
said inspecting device further includes
a detection delay part for delaying the time of arrival of said detection pulsed light at said detector relatively to the time of arrival of said electromagnetic wave at said detector.

6. The inspecting device according to claim 1, wherein said measurement delay part gives delay time to said probe light for delaying the time of arrival of said probe light at said inspecting target with respect to said pump light, the delay time being changed at a predetermined time width during inspection of the inspecting target and said predetermined time width being variable.

7. An inspecting method comprising the steps of:
   (a) irradiating an inspecting target with pump light;
   (b) scanning a scanned and observed area, which is larger than an irradiated area being irradiated with said pump light in said step (a), with probe light having the same pulse period as said pump light, an area which is not irradiated with said pump light being also observed in addition to the irradiated area;
   (c) detecting an electromagnetic wave generated from said inspecting target by irradiating said inspecting target with said probe light in said step (b);
   (d) delaying the time of arrival of said probe light at said inspecting target relatively to said pump light; and
   (e) applying a reverse bias voltage to said inspecting target, wherein
   a diameter of said probe light spot is smaller than a diameter of said pump light spot, and
   the reverse bias voltage applied by said reverse bias voltage applying part is variable.

* * * * *